United States Patent
Al-Shammari et al.

(10) Patent No.: US 10,604,496 B2
(45) Date of Patent: Mar. 31, 2020

(54) SYSTEMS AND METHODS RELATED TO THE PRODUCTION OF ETHYLENE OXIDE, ETHYLENE GLYCOL, AND/OR ETHANOLAMINES

(71) Applicant: SABIC Global Technologies B.V., Bergen op Zoom (NL)

(72) Inventors: Talal Al-Shammari, Riyadh (SA); Khalid Karim, Riyadh (SA); Zeeshan Nawaz, Riyadh (SA); Ali Al-Hammad, Riyadh (SA); Shehzada Khurram, Riyadh (SA); Mubarik Ali Bashir, Riyadh (SA); Labeeb Chaudhary Ahmed, Riyadh (SA); Abdullah Turki Al-Jaloud, Riyadh (SA); Saud Al-Khudeer, Riyadh (SA); Thabet Al-Qahtani, Riyadh (SA)

(73) Assignee: SABIC Global Technologies B.V., Bergen op Zoom (NL)

( * ) Notice: Subject to any disclaimer, the term of this patent is extended or adjusted under 35 U.S.C. 154(b) by 56 days.

(21) Appl. No.: 15/554,922

(22) PCT Filed: Mar. 2, 2016

(86) PCT No.: PCT/IB2016/051172
§ 371 (c)(1),
(2) Date: Aug. 31, 2017

(87) PCT Pub. No.: WO2016/139594
PCT Pub. Date: Sep. 9, 2016

(65) Prior Publication Data
US 2018/0044308 A1 Feb. 15, 2018

Related U.S. Application Data

(60) Provisional application No. 62/128,598, filed on Mar. 5, 2015.

(51) Int. Cl.
C07D 301/03 (2006.01)
C07D 301/32 (2006.01)
(Continued)

(52) U.S. Cl.
CPC .......... *C07D 301/03* (2013.01); *C07C 1/0485* (2013.01); *C07C 5/32* (2013.01);
(Continued)

(58) Field of Classification Search
CPC ...... C07D 301/10; C07D 301/00; C10G 2/32; C07C 209/60; C07C 213/04;
(Continued)

(56) References Cited

U.S. PATENT DOCUMENTS 3,849,262 A    11/1974  Cocuzza
3,914,332 A    10/1975  Dickason
(Continued)

FOREIGN PATENT DOCUMENTS

EP         1035094 A1       9/2000
WO    WO-2006/114417 A2    11/2006
(Continued)

OTHER PUBLICATIONS

Lui et al., gas generated by Fischer-Tropsch synthesis, CN 103626898 (machine translation), Mar. 2014.*
(Continued)

*Primary Examiner* — Jafar F Parsa
(74) *Attorney, Agent, or Firm* — Ballard Spahr LLP

(57) ABSTRACT

Disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from
(Continued)

the first C2 hydrocarbon stream, thereby producing a second C2 hydrocarbon stream; d) converting at least a portion of the ethane in the second C2 hydrocarbon stream to a second ethylene product; and e) producing ethylene oxide from at least a portion of the second ethylene product.

14 Claims, 5 Drawing Sheets

(51) Int. Cl.

| | | |
|---|---|---|
| C07C 213/04 | (2006.01) | |
| C07C 29/10 | (2006.01) | |
| C07C 1/04 | (2006.01) | |
| C07C 5/32 | (2006.01) | |
| C07C 9/06 | (2006.01) | |
| C07C 11/04 | (2006.01) | |
| C07C 31/20 | (2006.01) | |
| C07C 215/08 | (2006.01) | |
| C10G 2/00 | (2006.01) | |

(52) U.S. Cl.
CPC ............... *C07C 5/321* (2013.01); *C07C 9/06* (2013.01); *C07C 11/04* (2013.01); *C07C 29/106* (2013.01); *C07C 31/202* (2013.01); *C07C 213/04* (2013.01); *C07C 215/08* (2013.01); *C07D 301/32* (2013.01); *C10G 2/00* (2013.01)

(58) Field of Classification Search
CPC . C07C 209/106; C07C 31/202; C07C 209/16; C07C 209/86
See application file for complete search history.

(56) References Cited

U.S. PATENT DOCUMENTS

| | | | |
|---|---|---|---|
| 4,088,671 A | 5/1978 | Kobylinski | |
| 4,207,248 A | 6/1980 | Butter et al. | |
| 5,069,794 A | 12/1991 | Haag et al. | |
| 5,414,147 A | 5/1995 | Koga | |
| 5,785,739 A | 7/1998 | Baker | |
| 5,791,161 A | 8/1998 | Manley | |
| 5,990,370 A | 11/1999 | Sims | |
| 6,156,950 A | 12/2000 | Ragil et al. | |
| 6,338,791 B1 | 1/2002 | Ragil et al. | |
| 6,818,333 B2 | 11/2004 | Chau et al. | |
| 7,417,173 B2 | 8/2008 | Crone et al. | |
| 7,554,002 B2 | 6/2009 | Pham Duc | |
| 7,638,675 B2 | 12/2009 | Shecterle et al. | |
| 7,855,234 B2 | 12/2010 | Hoek et al. | |
| 2008/0141713 A1* | 6/2008 | Verma ................ | C07C 7/005 62/630 |
| 2010/0087684 A1* | 4/2010 | Do ...................... | C07C 209/16 564/478 |
| 2011/0137053 A1* | 6/2011 | Chewter ............. | C07D 301/08 549/523 |
| 2013/0062253 A1 | 3/2013 | Timken | |
| 2013/0224808 A1 | 8/2013 | Bell et al. | |

FOREIGN PATENT DOCUMENTS

| | | |
|---|---|---|
| WO | WO-2010/042168 A2 | 4/2010 |
| WO | WO-2011/057976 A2 | 5/2011 |
| WO | WO-2014/001354 A1 | 1/2014 |
| WO | WO-2016/139594 A1 | 9/2016 |

OTHER PUBLICATIONS

Sanfilippo, D. et al., Fluidized Bed Reactors for Paraffins Dehydrogenation. Chem Eng Sci. 1992; 47(9-11):2313-8.
International Search Report and Written Opinion dated Jun. 1, 2016 by the International Searching Authority for Patent Application No. PCT/IB2016/051172, which was filed on Mar. 2, 2016 and published as WO 2016/139594 on Sep. 9, 2016 (Inventor—Al-Shammari et al.; Applicant—SABIC Global Technologies B.V.; (10 pages).

* cited by examiner

SYSTEMS AND METHODS RELATED TO THE PRODUCTION OF ETHYLENE OXIDE, ETHYLENE GLYCOL, AND/OR ETHANOLAMINES

CROSS-REFERENCE TO RELATED APPLICATIONS

This is a U.S. National Phase Application of International Application No. PCT/IB2016/051172, filed Mar. 2, 2016, which claims the benefit of U.S. Provisional Application No. 62/128,598, filed Mar. 5, 2015, which are both incorporated herein by reference in their entirety.

BACKGROUND

Syngas (mixtures of $H_2$ and CO) can be readily produced from either coal or methane (natural gas) by methods well known in the art and widely commercially practiced around the world. A number of well-known industrial processes use syngas for producing various oxygenated organic chemicals.

The Fischer-Tropsch catalytic process for catalytically producing hydrocarbons from syngas was initially discovered and developed in the 1920's, and was used in South Africa for many years to produce gasoline range hydrocarbons as automotive fuels. The catalysts typically comprised iron or cobalt supported on alumina or titania, and promoters, like rhenium, zirconium, manganese, and the like were sometimes used with cobalt catalysts, to improve various aspects of catalytic performance. The products were typically gasoline-range hydrocarbon liquids having six or more carbon atoms, along with heavier hydrocarbon products.

Today lower molecular weight C1-C5 hydrocarbons (paraffins and/or olefins) are desired and can be obtained from syngas gas via Fischer-Tropsch catalytic process. There is a need to convert the paraffins and/or olefins obtained into other useful compound(s).

Accordingly, there remains a long-term market need for new and improved methods for producing useful compound(s) from syngas via intermediate low molecular weight C1-C5 hydrocarbons, such as from C2 hydrocarbons.

Accordingly, systems and methods useful for the production of ethylene oxide, ethylene glycol, and/or ethanolamines are described herein.

SUMMARY OF THE INVENTION

Disclosed herein is a system comprising: a) a Fischer-Tropsch reactor comprising a first inlet and a first outlet; b) a deethanizer comprising a second inlet and a second outlet; c) an olefin separator comprising a third inlet and a third outlet; d) an ethane cracker comprising a fourth inlet and a fourth outlet or an ethane dehydrogenator comprising a fifth inlet and a fifth outlet; e) an ethylene oxide reactor comprising a sixth inlet and a sixth outlet, wherein the Fischer-Tropsch reactor is in fluid communication with the deethanizer via a first connector, wherein the first connector is connected to the first outlet of the Fischer-Tropsch reactor and to the second inlet of the deethanizer, wherein the deethanizer is in fluid communication with the olefin separator via a second connector, wherein the second connector is connected to the second outlet of the deethanizer and to the third inlet of the olefin separator, wherein the olefin separator is in fluid communication with the ethane cracker or the ethane dehydrogenator via a third connector, wherein the third connector is connected to the third outlet of the olefin separator and to the fourth inlet of the ethane cracker or to the fifth inlet of the ethane dehydrogenator, wherein the ethane cracker or the ethane dehydrogenator is in fluid communication with the ethylene oxide reactor via a fourth connector, wherein the fourth connector is connected to the fourth outlet of the ethane cracker or to the fifth outlet of the ethane dehydrogenator and to the sixth inlet of the ethylene oxide reactor.

Also disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the first C2 hydrocarbon stream, thereby producing a second C2 hydrocarbon stream; d) converting at least a portion of the ethane in the second C2 hydrocarbon stream to a second ethylene product; and e) producing ethylene oxide from at least a portion of the second ethylene product.

Also disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the C2 hydrocarbon stream, thereby producing a second C2 hydrocarbon stream; d) converting at least a portion of the ethane in the second C2 hydrocarbon stream to a second ethylene product; e) combining at least a portion of the first ethylene product and at least a portion of the second ethylene product, thereby producing a third ethylene product; and f) producing ethylene oxide from at least a portion of the third ethylene product.

In one aspect, the method can further comprise producing ethylene glycol from at least a portion of the ethylene oxide.

In one aspect, the method can further comprise producing one or more ethanolamines from at least a portion of the ethylene oxide.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

The accompanying figures, which are incorporated in and constitute a part of this specification, illustrate several aspects, and together with the description, serve to explain the principles of the invention.

Figure 1:
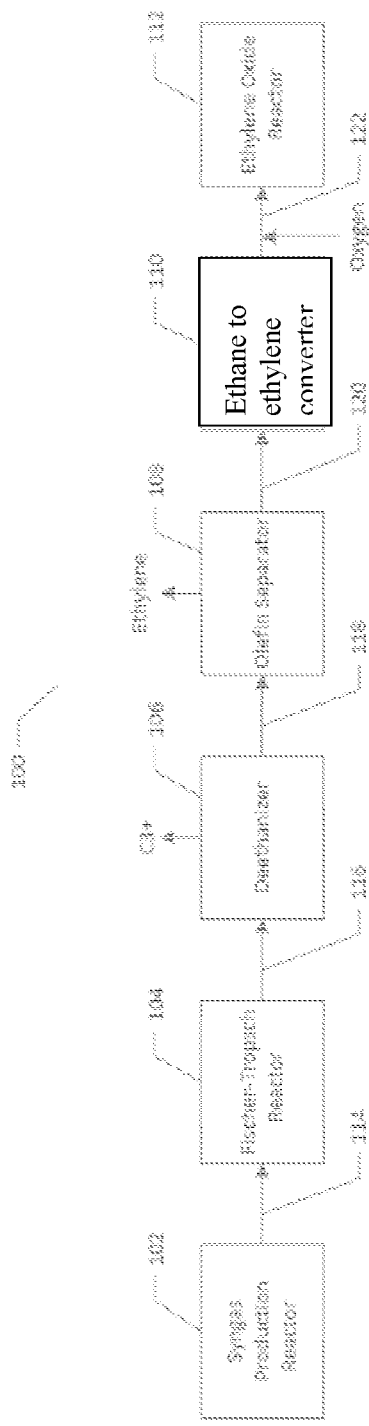
FIG. 1 shows a flow diagram of a method and system disclosed herein.

Additional advantages of the invention will be set forth in part in the description that follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are materials, compounds, compositions, and components that can be used for, can be used in conjunction with, can be used in preparation for, or are products of the disclosed method and compositions. It is to be understood that when combinations, subsets, interactions, groups, etc. of these materials are disclosed that while specific reference of each various individual and collective combinations and permutation of these compounds cannot be explicitly disclosed, each is specifically contemplated and described herein. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

1. Definitions

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "a hydrocarbon" includes mixtures of hydrocarbons.

The term "one or more ethanolamines" refers to a composition comprising monoethanolamine, diethanolamine, or triethanolamine, or a combination thereof.

Ranges can be expressed herein as from " " one particular value, and/or to " " another particular value. When such a range is expressed, another aspect includes from the one particular value and/or to the other particular value. Similarly, when values are expressed as approximations, by use of the antecedent "," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such a ratio regardless of whether additional components are contained in the compound.

A weight percent of a component, unless specifically stated to the contrary, is based on the total weight of the formulation or composition in which the component is included.

2. Fischer-Tropsch Catalytic Process

The Fischer-Tropsch catalytic process for producing hydrocarbons from syngas is known in the art. Several reactions can take place in a Fischer-Tropsch process, such as, a Fischer-Tropsch (FT) reaction, a water gas shift reaction, and a hydrogen methanation, as shown in Scheme 1.

Scheme 1

FT reaction:

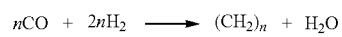

Water Gas Shift Reaction (WGS):

Methanation:

The gases that are being mixed in the Fischer-Tropsch process described herein comprise $H_2$ and CO. The $H_2/CO$ molar ratio of the feed gas can be from 0.5 to 4. For example, the $H_2/CO$ molar ratio can be from 1.0 to 3.0, such as, for example, from 1.5 to 3.0, or in another example, from 1.5 to 2.5. It will be appreciated that the $H_2/CO$ molar ratio can control the selectivity of the hydrocarbons that are being produced. The consumption molar ratio of $H_2/CO$ is usually from about 1.0 to about 2.5, such as for example, from about 1.5 to 2.1, this ratio increases as long as the water gas shift reaction is active and, thus, the use of a feed ratio below the consumption ratio will result in a stable $H_2/CO$ ratio during the reaction within an acceptable range (normally below 2). The $H_2$ and CO are catalytically reacted in a Fischer-Tropsch reaction.

A Fischer-Tropsch process that targets the production of light olefins (C2-C10 olefins) is desired and such process can produce a significant amount of a hydrocarbon stream comprising a C2 hydrocarbon stream comprising ethane and ethylene. As disclosed herein, a hydrocarbon stream comprising a C2 hydrocarbon stream undergo processing to be converted into ethylene oxide, which can be further converted into ethylene glycol or one or more ethanolamines. Ethylene oxide is one of the most important raw materials used in the large-scale chemical production. Ethylene oxide can be used for synthesis of ethylene glycol. Furthermore, ethylene glycol is useful as an antifreeze, in the production of polyester and polyethylene terephthalate (PET), liquid coolants, and solvents. Ethanolamine is useful as feedstock in the production of detergents, emulsifiers, polishes, pharmaceuticals, corrosion inhibitors, and other chemical intermediates. The system and method disclosed herein are capable of producing ethylene oxide, ethylene glycol, and one or more ethanolamines from a hydrocarbon stream produced in a Fischer-Tropsch Process.

3. System

Disclosed herein is a system comprising: a) a Fischer-Tropsch reactor comprising a first inlet and a first outlet; b) a deethanizer comprising a second inlet and a second outlet;

c) an olefin separator comprising a third inlet and a third outlet; d) an ethane cracker comprising a fourth inlet and a fourth outlet or an ethane dehydrogenator comprising a fifth inlet and a fifth outlet; e) an ethylene oxide reactor comprising a sixth inlet and a sixth outlet, wherein the Fischer-Tropsch reactor is in fluid communication with the deethanizer via a first connector, wherein the first connector is connected to the first outlet of the Fischer-Tropsch reactor and to the second inlet of the deethanizer, wherein the deethanizer is in fluid communication with the olefin separator via a second connector, wherein the second connector is connected to the second outlet of the deethanizer and to the third inlet of the olefin separator, wherein the olefin separator is in fluid communication with the ethane cracker or the ethane dehydrogenator via a third connector, wherein the third connector is connected to the third outlet of the olefin separator and to the fourth inlet of the ethane cracker or to the fifth inlet of the ethane dehydrogenator, wherein the ethane cracker or the ethane dehydrogenator is in fluid communication with the ethylene oxide reactor via a fourth connector, wherein the fourth connector is connected to the fourth outlet of the ethane cracker or to the fifth outlet of the ethane dehydrogenator and to the sixth inlet of the ethylene oxide reactor.

In one aspect, the system comprises an ethane cracker.

In one aspect, the system comprises an ethane dehydrogenator.

In one aspect, the system further comprises an ethylene glycol reactor comprising a seventh inlet, wherein the ethylene glycol reactor is in fluid communication with the ethylene oxide reactor via a fifth connector, wherein the fifth connector is connected to the sixth outlet of the ethylene oxide reactor and the seventh inlet of the ethylene glycol reactor.

In one aspect, the system further comprises a syngas production reactor comprising an eighth outlet, wherein the syngas production reactor is in fluid communication with the Fischer-Tropsch reactor via sixth connector, wherein the Fischer-Tropsch reactor further comprises a ninth inlet, wherein the sixth connector is connected to the eighth outlet of the syngas production reactor and to the ninth inlet of the Fischer-Tropsch reactor.

In one aspect, the system further comprises an ethanolamine reactor comprising a tenth inlet, wherein the ethanolamine reactor is in fluid communication with the ethylene oxide reactor via an eighth connector, wherein the eighth connector is connected to the sixth outlet of the ethylene oxide reactor and the tenth inlet of the ethanolamine reactor.

In one aspect, the olefin separator is in fluid communication with the ethylene oxide reactor via a seventh connector. In one aspect, the seventh connector is connected to a ninth outlet of the olefin reactor and a tenth inlet of ethylene oxide reactor.

Isothermal and/or adiabatic fixed, moving, or fluidized bed reactors can be used as a Fischer-Tropsch reactor, which can carry out the Fischer-Tropsch process selective to the production of olefins. The Fischer-Tropsch reactor is configured to convert syngas to olefins.

The Fischer-Tropsch reactor can comprise one or more Fischer-Tropsch catalysts. Fischer-Tropsch catalysts are known in the art and can, for example, be Fe based catalysts and/or Co based catalysts and/or Ru based catalysts. Such catalysts are described in U.S. Pat. Nos. 4,088,671 and 4,207,248, which are incorporated herein by their entirety, specifically for their disclosure regarding Fischer-Tropsch catalysts.

A deethanizer is known in the art. A deethanizer separates the C2 hydrocarbon stream, disclosed herein, from the hydrocarbon stream disclosed herein. A deethanizer can be a fractionation column, which uses distillation separation technologies for hydrocarbon separation. Dethanizers are, for example, described in U.S. Pat. No. 7,554,002, European Patent 1035094, and U.S. Pat. No. 5,791,161, which are incorporated herein by their entirety, specifically for their disclosure regarding deethanizers.

An ethane to ethylene converter can be an ethane cracker or a dehydrogenator.

A dehydrogenation reactor is a vessel that is configured to convert alkanes (i.e. paraffins) to alkenes (i.e. olefins). For example, the dehydrogenation reactor can be a fixed bed tubular or tube bundle reactor. The conversion of alkanes (i.e. paraffins) to alkenes (i.e. olefins) is often a catalytic process. For example, a dehydrogenation reactor can convert ethane into ethylene. The dehydrogenation reactor can further comprise a dehydrogenation catalyst, such as, for example, a Pd or V based catalyst.

In one aspect, the catalytic process can, for example, be nonoxidative as described in U.S. Pat. No. 7,417,173. The nonoxidative catalytic ethane dehydrogenation can be carried out under heterogeneous catalysis in a fluidized bed, as described in Chem. Eng. Sci. 1992 b, 47 (9-11) 2313. Appropriately, two fluidized beds can be operated in parallel, of which one is generally in the state of regeneration. The working pressure is typically from 1 to 2 bar, the dehydrogenation temperature generally from 550 to 600° C., The heat required for the dehydrogenation is introduced into the reaction system by preheating the dehydrogenation catalyst to the reaction temperature.

In another aspect, the dehydrogenation can be oxidative. Dehydrogenation catalysts such as V based catalysts are, for example, described in U.S. Pat. No. 3,914,332, which is hereby incorporated by reference, specifically for the disclosure regarding oxidative catalysts.

An ethane cracker a reactor that is configured to heat up ethane to thermally break apart ethane to form ethylene. An ethane cracker is known in the art. An ethane cracker can for example be a steam cracker. Ethane crackers and steam crackers are, for example, described in U.S. Pat. Nos. 5,990,370, and 5,785,739, which are incorporated herein by their entirety, specifically for their disclosure regarding ethane crackers and steam crackers.

An olefin separator is a separator that can separate olefins from paraffins and other products. The olefin separator can be a separator that cryogenically can separate olefins from paraffins and other products. For example, the olefin separator can separate ethylene from a C2 hydrocarbon stream. Olefin separators are known in the art and can also include distillation and membrane separation, or a combination thereof.

An ethylene oxide reactor is a vessel that is configured to carry out a reaction to produce ethylene oxide from ethylene. For example, ethylene oxide can be produced from a reaction of ethylene and oxygen ($O_2$) in a direct oxidation reaction. In another example, ethylene oxide can be produced from a reaction of ethylene and chlorohydrin. These types of reactions are known in the art.

An ethylene glycol reactor is a vessel that is configured to carry a reaction to produce ethylene glycol from ethylene oxide. Ethylene glycol can be produced by a reaction of ethylene oxide and water. It is understood that ethylene glycol can comprise monoethylene glycol, diethylene glycol, triethylene glycol, tetraethylene glycol, or polyethylene glycol, or a combination thereof which are obtained by the reaction of ethylene oxide and water. In one aspect, the ethylene glycol is monoethylene glycol. In another aspect, the ethylene glycol is substantially monoethylene glycol.

An ethanolamine reactor is a vessel that is configured to carry out a reaction to produce one or more ethanolamines from ethylene oxide. One or more ethanolamines are typically produced by a reaction of ethylene oxide and ammonia. An ethanolamine reactor is known in the art. For example, PCT Publication Number WO 2006/114417 discloses a method in which ethylene oxide (EO) is continuously reacted with ammonia to obtain a reaction product containing monoethanolamine (MEOA), diethanolamine (DEOA), and triethanolamine (TEOA) at a weight ratio MEOA:DEOA:TEOA=80-94:5.9-15:0.1-5. PCT Publication Number WO 2006/114417 is hereby incorporated by reference, specifically for its disclosure related to ethanolamine production.

A syngas production reactor can produce syngas from one or more sources. Syngas can be produced from many sources, including natural gas, coal, biomass, or virtually any hydrocarbon feedstock, by reaction with steam or oxygen. For example, partial oxidation (POX) of methane (or hydrocarbons) is a non-catalytic, large-scale process to make syngas and yields syngas with $H_2/CO$ ratio of about 2. In another example, the syngas reactor can convert natural gas into syngas. As such, the syngas production reactor can be an autothermal reforming (ATR) reactor which combines methane and steam reforming and oxidation in one process. The heat needed for reforming is generated inside the reactor by oxidization of the feed gas (natural gas). ATR is also suitable for large-scale production of syngas for gas-to-liquids or large-scale methanol synthesis processes.

Optionally, in various aspects, the disclosed system can be operated or configured on an industrial scale. In one aspect, the reactors described herein can each be an industrial size reactor. For example, the Fischer-Tropsch reactor can be an industrial size reactor. In another example, the deethanizer can be an industrial size reactor. In yet another example, the dehydrogenation reactor can be an industrial size reactor. In yet another example, the olefin separator can be an industrial size reactor. In yet another example, the dehydrogenator can be an industrial size reactor. In yet another example, the ethane cracker can be an industrial size reactor. In yet another example, the ethylene oxide reactor can be an industrial size reactor. In yet another example, the ethylene glycol reactor can be an industrial size reactor. In yet another example, the ethanolamine reactor can be an industrial size reactor. In yet another example, the syngas production reactor can be an industrial size reactor.

The reactors disclosed herein can have a volume of at least 1,000 liters, 2,000 liters, 5,000 liters, or 20,000 liters. For example, the reactor can have a volume from 1,000 liter to 20,000 liters.

In one aspect, the Fischer-Tropsch reactor can have a volume of at least 1,000 liters, 2,000 liters, 5,000 liters, or 20,000 liters. For example, Fischer-Tropsch reactor can have a volume from 1,000 liter to 20,000 liters.

In one aspect, the deethanizer can have a volume of at least 1,000 liters, 2,000 liters, 5,000 liters, or 20,000 liters. For example, deethanizer can have a volume from 1,000 liter to 20,000 liters.

In one aspect, the olefin separator can have a volume of at least 1,000 liters, 2,000 liters, 5,000 liters, or 20,000 liters. For example, the olefin separator can have a volume from 1,000 liter to 20,000 liters.

In one aspect, the ethane cracker can have a volume of at least 1,000 liters, 2,000 liters, 5,000 liters, or 20,000 liters. For example, the ethane cracker can have a volume from 1,000 liter to 20,000 liters.

In one aspect, the dehydrogenator can have a volume of at least 1,000 liters, 2,000 liters, 5,000 liters, or 20,000 liters. For example, the dehydrogenator can have a volume from 1,000 liter to 20,000 liters.

In one aspect, the ethylene oxide reactor can have a volume of at least 1,000 liters, 2,000 liters, 5,000 liters, or 20,000 liters. For example, the ethylene oxide reactor can have a volume from 1,000 liter to 20,000 liters.

In one aspect, the ethylene glycol reactor can have a volume of at least 1,000 liters, 2,000 liters, 5,000 liters, or 20,000 liters. For example, the ethylene glycol reactor can have a volume from 1,000 liter to 20,000 liters.

In one aspect, the ethanolamine reactor can have a volume of at least 1,000 liters, 2,000 liters, 5,000 liters, or 20,000 liters. For example, the ethanolamine reactor can have a volume from 1,000 liter to 20,000 liters.

In one aspect, the syngas production reactor can have a volume of at least 1,000 liters, 2,000 liters, 5,000 liters, or 20,000 liters. For example, the syngas production reactor can have a volume from 1,000 liter to 20,000 liters.

In one aspect, the system is capable of producing at least about 100 liters, 250 liters, 500 liters, 1,000 liters, or from about 100 liters to about 1,000 liters of ethylene oxide per hour.

In one aspect, the system is capable of producing at least about 100 liters, 250 liters, 500 liters, 1,000 liters, or from about 100 liters to about 1,000 liters of ethylene glycol per hour.

In one aspect, the system is capable of producing at least about 50 liters, 100 liters, 250 liters, 500 liters, 1,000 liters, or from about 50 liters to about 1,000 liters of one or more ethanolamines per hour.

Now referring to FIG. 1, which shows a non-limiting exemplary aspect of the system and method disclosed herein. FIG. 1 shows a system (100). The system has a syngas production reactor (102). The syngas production reactor (102) is in fluid communication with a Fischer-Tropsch reactor (104). The Fischer-Tropsch reactor (104) is in further fluid communication with a deethanizer (106). The deethanizer (106) is in further fluid communication with an olefin separator (108). The olefin separator (108) is in further fluid communication with a dehydrogenator (110). The dehydrogenation reactor (110) is in further fluid communication with an ethylene oxide reactor (112). The syngas production reactor (102) is in fluid communication with a Fischer-Tropsch reactor (104) via a sixth connector (114). The Fischer-Tropsch reactor (104) is in further fluid communication with a deethanizer (106) via a first connector (116). The deethanizer (106) is in further fluid communication with an olefin separator (108) via a second connector (118). The olefin separator (108) is in further fluid communication with an ethane to ethylene converter (such as an ethane cracker or dehydrogenator) (110) via a third connector (120). The ethylene converter (such as an ethane cracker or dehydrogenator) (110) is in further fluid communication with an ethylene oxide reactor (112) via a fourth connector (122).

Figure 2:
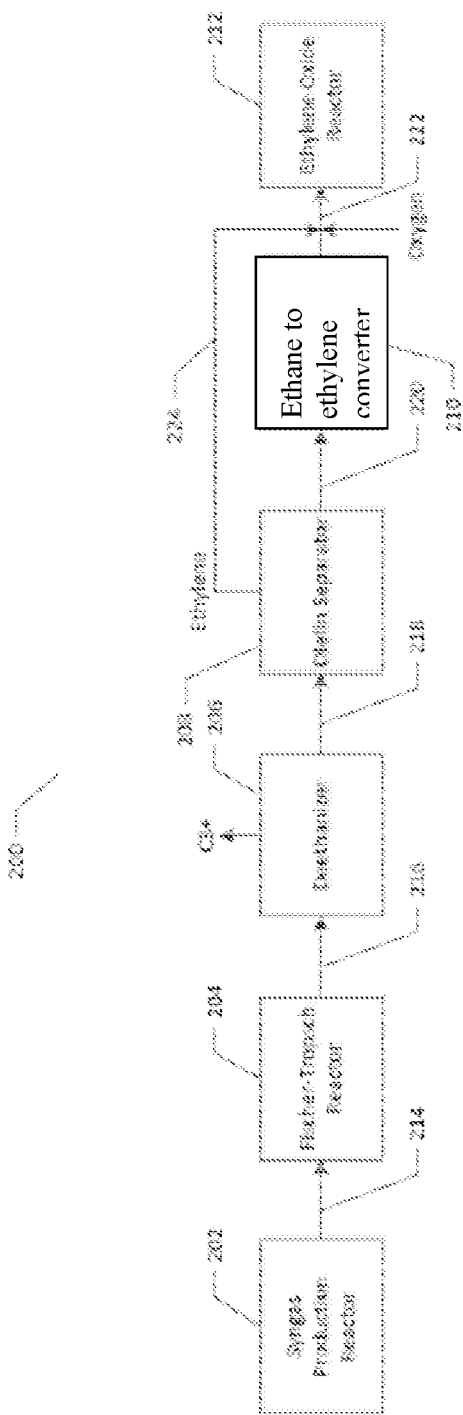
FIG. 2 shows a flow diagram of a method and system disclosed herein.

Now referring to FIG. 2, which shows a non-limiting exemplary aspect of the system and method disclosed herein. FIG. 2 shows a system (200). The system has a syngas production reactor (202). The syngas production reactor (202) is in fluid communication with a Fischer-Tropsch reactor (204). The Fischer-Tropsch reactor (204) is in further fluid communication with a deethanizer (206). The deethanizer (206) is in further fluid communication with an olefin separator (208). The olefin separator (208) is in further fluid communication with an ethylene converter (such as an ethane cracker or dehydrogenator) (210). The ethylene converter (such as an ethane cracker or dehydrogenator) (210) is in further fluid communication with an ethylene oxide reactor (212). The syngas production reactor (202) is in fluid communication with a Fischer-Tropsch reactor (204) via a sixth connector (214). The Fischer-Tropsch reactor (204) is in further fluid communication with a deethanizer (206) via a first connector (216). The deethanizer (206) is in further fluid communication with an olefin separator (208) via a second connector (218). The olefin separator (208) is in further fluid communication with an ethane to ethylene converter (such as an ethane cracker or dehydrogenator) (210) via a third connector (220). The ethane to ethylene converter (such as an ethane cracker or dehydrogenator) (210) is in further fluid communication with an ethylene oxide reactor (212) via a fourth connector (222). The olefin separator (208) is in further fluid communication with the ethylene oxide reactor (212) via a seventh connector (224).

Figure 3:
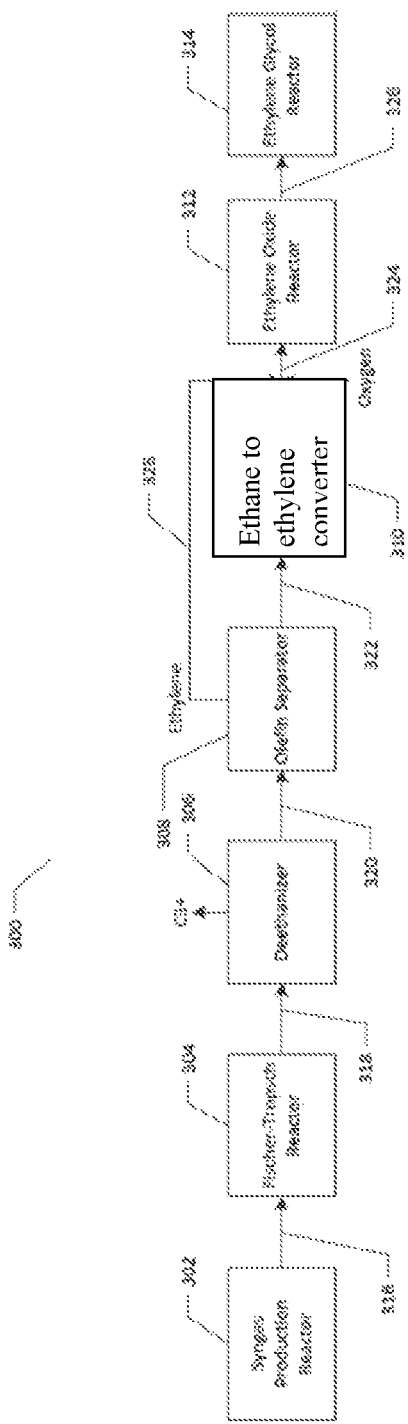
FIG. 3 shows a flow diagram of a method and system disclosed herein.

Now referring to FIG. 3, which shows a non-limiting exemplary aspect of the system and method disclosed herein. FIG. 3 shows a system (300). The system has a syngas production reactor (302). The syngas production reactor (302) is in fluid communication with a Fischer-Tropsch reactor (304). The Fischer-Tropsch reactor (304) is in further fluid communication with a deethanizer (306). The deethanizer (306) is in further fluid communication with an olefin separator (308). The olefin separator (308) is in further fluid communication with an ethylene converter (such as an ethane cracker or dehydrogenator) (310). The ethane to ethylene converter (such as an ethane cracker or dehydrogenator) (310) is in further fluid communication with an ethylene oxide reactor (312). The ethylene oxide reactor (312) is in further fluid communication with an ethylene glycol reactor (314). The syngas production reactor (302) is in fluid communication with a Fischer-Tropsch reactor (304) via a sixth connector (316). The Fischer-Tropsch reactor (304) is in further fluid communication with a deethanizer (306) via a first connector (318). The deethanizer (306) is in further fluid communication with an olefin separator (308) via a second connector (320). The olefin separator (308) is in further fluid communication with an ethane to ethylene converter (such as an ethane cracker or dehydrogenator) (310) via a third connector (322). The ethane to ethylene converter (such as an ethane cracker or dehydrogenator) (310) is in further fluid communication with an ethylene oxide reactor (312) via a fourth connector (324). The ethylene oxide reactor (312) is in further fluid communication with an ethylene glycol reactor (314) via a fifth connector (326). The olefin separator (308) is in further fluid communication with the ethylene oxide reactor (312) via a seventh connector (328).

Figure 4:
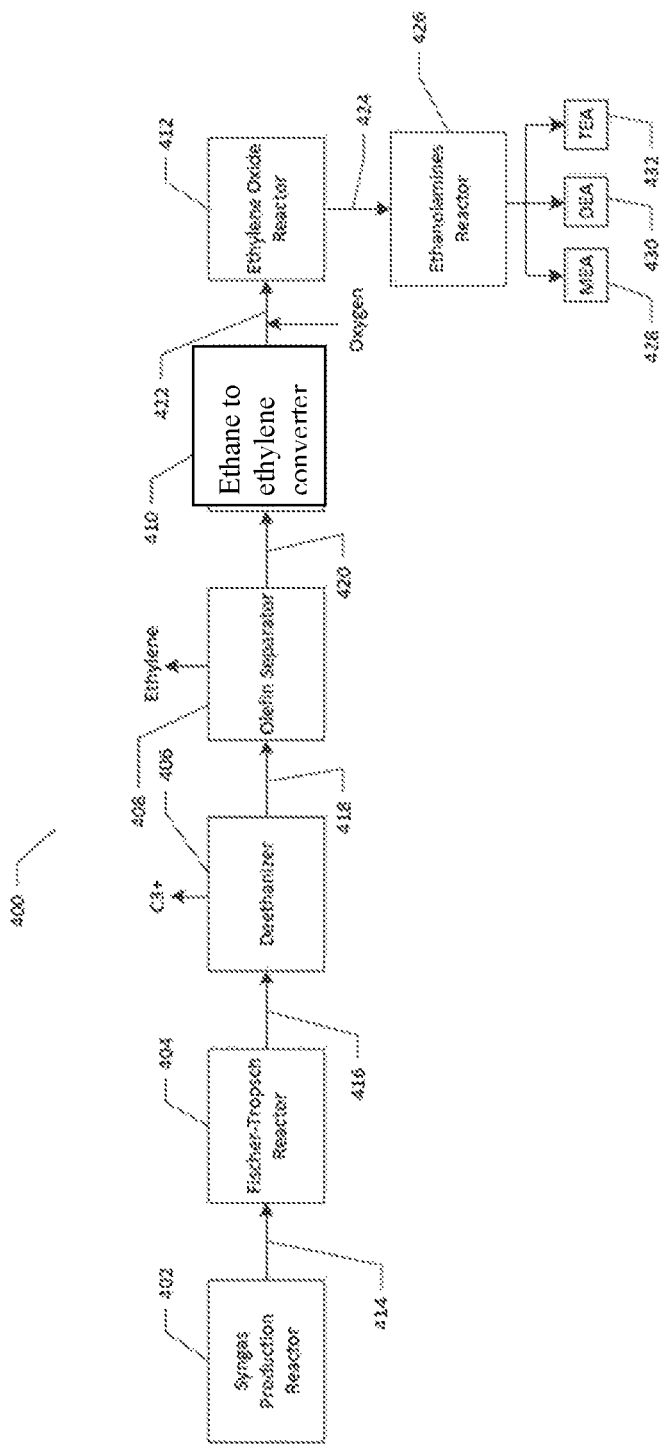
FIG. 4 shows a flow diagram of a method and system disclosed herein.

Now referring to FIG. 4, which shows a non-limiting exemplary aspect of the system and method disclosed herein. FIG. 4 shows a system (400). The system has a syngas production reactor (402). The syngas production reactor (402) is in fluid communication with a Fischer-Tropsch reactor (404). The Fischer-Tropsch reactor (404) is in further fluid communication with a deethanizer (406). The deethanizer (406) is in further fluid communication with an olefin separator (408). The olefin separator (408) is in further fluid communication with an ethane to ethylene converter (such as an ethane cracker or dehydrogenator) (410). The ethane to ethylene converter (such as an ethane cracker or dehydrogenator) (410) is in further fluid communication with an ethylene oxide reactor (412). The ethylene oxide reactor (412) is in further fluid communication with an ethanolamine reactor (426). The ethanolamine reactor (426) is in further fluid communication with a monoethanolamine holding tank (428). The ethanolamine reactor (426) is in further fluid communication with a diethanolamine holding tank (430). The ethanolamine reactor (426) is in further fluid communication with a triethanolamine holding tank (432). The syngas production reactor (402) is in fluid communication with a Fischer-Tropsch reactor (404) via a sixth connector (414). The Fischer-Tropsch reactor (404) is in further fluid communication with a deethanizer (406) via a first connector (416). The deethanizer (406) is in further fluid communication with an olefin separator (408) via a second connector (418). The olefin separator (408) is in further fluid communication with the ethane to ethylene converter (such as an ethane cracker or dehydrogenator) (410) via a third connector (420). The dehydrogenation reactor (410) is in further fluid communication with an ethylene oxide reactor (412) via a fourth connector (422). The ethylene oxide reactor (412) is in further fluid communication with an ethanolamine reactor (426) via an eighth connector (424).

Figure 5:
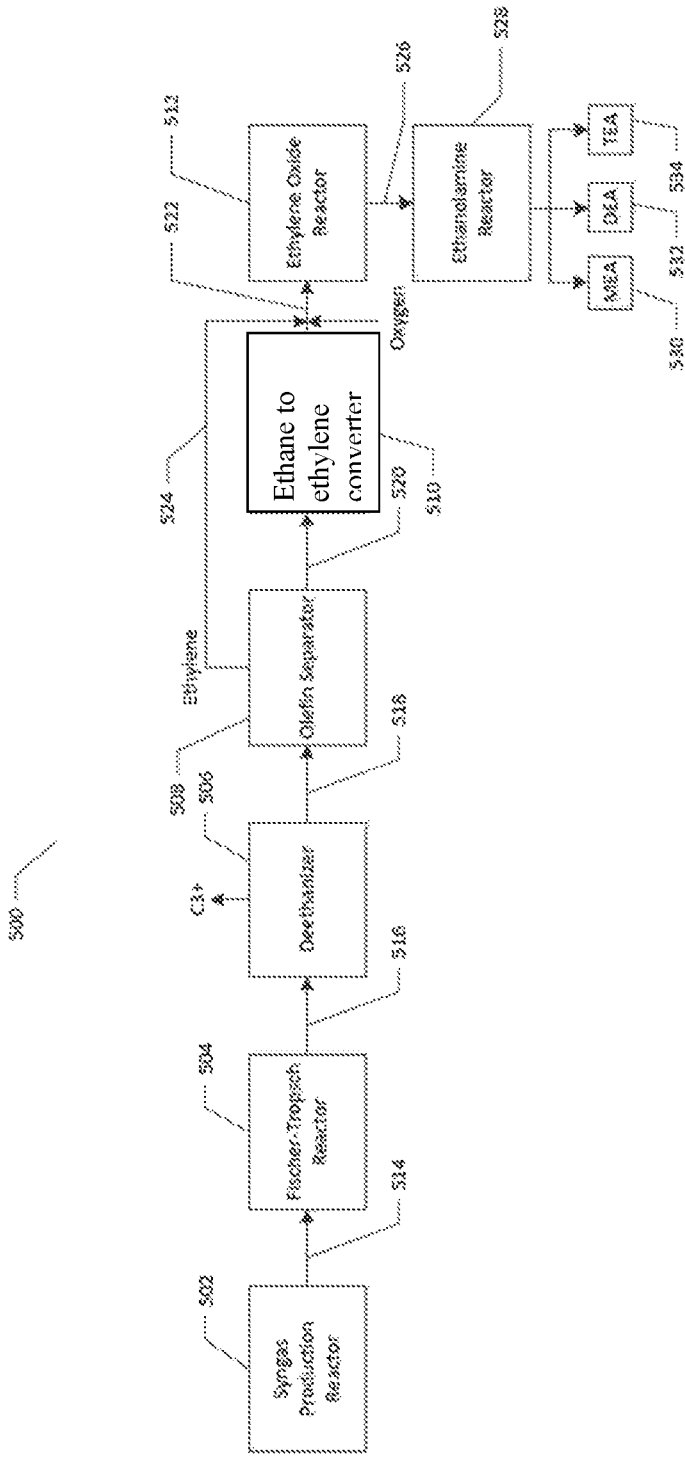
FIG. 5 shows a flow diagram of a method and system disclosed herein.

Now referring to FIG. 5, which shows a non-limiting, exemplary aspect of the system and method disclosed herein. FIG. 5 shows a system (500). The system has a syngas production reactor (502). The syngas production reactor (502) is in fluid communication with a Fischer-Tropsch reactor (504). The Fischer-Tropsch reactor (504) is in further fluid communication with a deethanizer (506). The deethanizer (506) is in further fluid communication with an olefin separator (508). The olefin separator (508) is in further fluid communication with an ethane to ethylene converter (such as an ethane cracker or dehydrogenator) (510). The ethane cracker (510) is in further fluid communication with an ethylene oxide reactor (512). The ethylene oxide reactor (512) is in further fluid communication with an ethanolamine reactor (528). The ethanolamine reactor (428) is in further fluid communication with a monoethanolamine holding tank (530). The ethanolamine reactor (528) is in further fluid communication with a diethanolamine holding tank (532). The ethanolamine reactor (528) is in further fluid communication with a triethanolamine holding tank (534). The syngas production reactor (502) is in fluid communication with a Fischer-Tropsch reactor (504) via a sixth connector (514). The Fischer-Tropsch reactor (504) is in further fluid communication with a deethanizer (506) via a first connector (516). The deethanizer (506) is in further fluid communication with an olefin separator (508) via a second connector (518). The olefin separator (508) is in further fluid communication with an ethane to ethylene converter (such as an ethane cracker or dehydrogenator) (510) via a third connector (520). The ethane to ethylene converter (such as an ethane cracker or dehydrogenator) (510) is in further fluid communication with an ethylene oxide reactor (512) via a fourth connector (522). The olefin separator (508) is in further fluid communication with the ethylene oxide reactor (512) via a seventh connector (524). The ethylene oxide reactor (512) is in further fluid communication with an ethanolamine reactor (528) via an eighth connector (526).

4. Methods

Also disclosed herein is a method of producing ethylene oxide. In one aspect, the method can further produce ethylene glycol. In one aspect, the method can further produce one or more ethanolamines. In one aspect, the method can be performed by the system disclosed herein.

Disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the first C2 hydrocarbon stream, thereby producing a second C2 hydrocarbon stream; d) converting at least a portion of the ethane in the second C2 hydrocarbon stream to a second ethylene product; and e) producing ethylene oxide from at least a portion of the second ethylene product. In one aspect, the method further comprises the step of producing ethylene glycol from at least a portion of the ethylene oxide. In one aspect, the method further comprises the step of producing one or more ethanolamines comprising monoethanolamine, diethanolamine, and/or triethanolamine from at least a portion of the ethylene oxide.

Also disclosed herein is a method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the C2 hydrocarbon stream, thereby producing a second C2 hydrocarbon stream; d) converting at least a portion of the ethane in the second C2 hydrocarbon stream to a second ethylene product; e) combining at least a portion of the first ethylene product and at least a portion of the second ethylene product, thereby producing a third ethylene product; and f) producing ethylene oxide from at least a portion of the third ethylene product. In one aspect, the method further comprises the step of producing ethylene glycol from at least a portion of the ethylene oxide. In one aspect, the method further comprises the step of producing one or more ethanolamines comprising monoethanolamine, diethanolamine, and/or triethanolamine from at least a portion of the ethylene oxide.

When the method comprises the step of producing one or more ethanolamines comprising monoethanolamine, diethanolamine, and/or triethanolamine from at least a portion of the ethylene oxide, the method, in one aspect, can further comprises the step of separating monoethanolamine from the one or more ethanolamines. When the method comprises the step of producing one or more ethanolamines comprising monoethanolamine, diethanolamine, and/or triethanolamine from at least a portion of the ethylene oxide, the method, in another aspect, can further comprises the step of separating diethanolamine from the one or more ethanolamines. When the method comprises the step of producing one or more ethanolamines comprising monoethanolamine, diethanolamine, and/or triethanolamine from at least a portion of the ethylene oxide, the method, in another aspect, can further comprise the step of separating triethanolamine from the one or more ethanolamines. Separation of monoethanolamine, diethanolamine, and triethanolamine is known in the art, such process is, for example, described in U.S. Pat. No. 3,849,262 to Cocuzza, which is hereby incorporated by reference for its disclosure of separation of monoethanolamine, diethanolamine, and triethanolamine from one or more ethanolamines (mixtures of monoethanolamine, diethanolamine, and triethanolamine).

In one aspect, the one or more ethanolamines comprises monoethanolamine, diethanolamine, and triethanolamine. In another aspect, the one or more ethanolamines comprises monoethanolamine. In yet another aspect, the one or more ethanolamines comprises diethanolamine. In yet another aspect, the one or more ethanolamines comprises triethanolamine.

In one aspect, the step of converting at least a portion of the ethane in the second C2 hydrocarbon stream to a second ethylene product comprises dehydrogenating the at least a portion of the ethane in the second C2 hydrocarbon stream.

In one aspect, the step of converting at least a portion the ethane in the second C2 hydrocarbon stream to a second ethylene product comprises cracking the at least a portion of the ethane in the second C2 hydrocarbon stream.

In one aspect, the step of producing ethylene oxide from at least a portion of the second ethylene product comprises reacting the second ethylene product with an oxygenate. In one aspect, the step of producing ethylene oxide from at least a portion of the third ethylene product comprises reacting the third ethylene product with an oxygenate. The oxygenate can be $H_2O$.

In one aspect, the hydrocarbon stream further comprises C3-C6 hydrocarbons, such as, C3-C6 olefins and paraffins. For example, the hydrocarbon stream can further comprise at least about 30 wt % of C3-C6 olefins and paraffins. In another example, the hydrocarbon stream can further comprise at least about 40 wt % of C3-C6 olefins and paraffins. In yet another example, the hydrocarbon stream can further comprise at least about 50 wt % of C3-C6 olefins and paraffins. In yet another example, the hydrocarbon stream can further comprise at least about 60 wt % of C3-C6 olefins and paraffins. In yet another example, the hydrocarbon stream can further comprise from about 30 wt % to about 70 wt % of C3-C6 olefins and paraffins.

In one aspect, the hydrocarbon stream further comprises C3-C10 hydrocarbons, such as, C3-C10 olefins and paraffins. For example, the hydrocarbon stream can further comprise at least about 30 wt % of C3-C10 olefins and paraffins. In another example, the hydrocarbon stream can further comprise at least about 40 wt % of C3-C10 olefins and paraffins. In yet another example, the hydrocarbon stream can further comprise at least about 50 wt % of C3-C10 olefins and paraffins. In yet another example, the hydrocarbon stream can further comprise at least about 60 wt % of C3-C10 olefins and paraffins. In yet another example, the hydrocarbon stream can further comprise from about 30 wt % to about 70 wt % of C3-C10 olefins and paraffins.

In one aspect, the hydrocarbon stream comprises at least about 5 wt % of a first C2 hydrocarbon stream comprising ethane and a first ethylene product. In one aspect, the hydrocarbon stream comprises at least about 10 wt % of a first C2 hydrocarbon stream comprising ethane and a first ethylene product. In another aspect, the hydrocarbon stream comprises at least about 15 wt % of a first C2 hydrocarbon stream comprising ethane and a first ethylene product. In yet another aspect, the hydrocarbon stream comprises at least about 20 wt % of a first C2 hydrocarbon stream comprising ethane and a first ethylene product. In yet another aspect, the hydrocarbon stream comprises at least about 25 wt % of a first C2 hydrocarbon stream comprising ethane and a first ethylene product. In yet another aspect, the hydrocarbon stream comprises at least about 30 wt % of a first C2 hydrocarbon stream comprising ethane and a first ethylene product.

In one aspect, the hydrocarbon stream comprises from about 5 wt % to about 30 wt % of the first C2 hydrocarbon stream comprising ethane and a first ethylene product. In another aspect, the hydrocarbon stream comprises from about 5 wt % to about 20 wt % of the first C2 hydrocarbon stream comprising ethane and a first ethylene product. In yet another aspect, the hydrocarbon stream comprises from about 5 wt % to about 15 wt of the first C2 hydrocarbon stream comprising ethane and a first ethylene product.

In one aspect, the first C2 hydrocarbon stream comprises at least about 30 wt % of ethane. In another aspect, the first C2 hydrocarbon stream comprises at least about 50 wt % of ethane. In yet another aspect, the first C2 hydrocarbon stream comprises at least about 70 wt % of ethane. For example, the first C2 hydrocarbon stream can comprise at least from about 30 wt % to about 70 wt % of ethane.

In one aspect, the first C2 hydrocarbon stream comprises at least about 30 wt % of the first ethylene product. In another aspect, the first C2 hydrocarbon stream comprises at least about 50 wt % of the first ethylene product. In yet another aspect, the first C2 hydrocarbon stream comprises at least about 70 wt % of the first ethylene product. For example, first C2 hydrocarbon stream can comprise at least from about 30 wt % to about 70 wt % of the first ethylene product.

In one aspect, the first C2 hydrocarbon stream comprises from about 20 wt % to about 70 wt % of ethane and from about 70 wt % to about 20 wt % of the first ethylene product.

The step of separating at least a portion of the first C2 hydrocarbon stream from the hydrocarbon stream can be performed by the deethanizer disclosed herein. In one aspect, at least about 60 wt % of the first C2 hydrocarbon stream in the hydrocarbon stream is separated from the hydrocarbon stream. In another aspect, at least about 80 wt % of the first C2 hydrocarbon stream in the hydrocarbon stream is separated from the hydrocarbon stream. In yet another aspect, from about 60 wt % to about 95 wt % of the first C2 hydrocarbon stream in the hydrocarbon stream is separated from the hydrocarbon stream.

The step of separating at least a portion of the first ethylene product from the first C2 hydrocarbon stream, thereby producing a second C2 hydrocarbon stream can be performed by the olefin separator disclosed herein. In one aspect, the second C2 hydrocarbon stream comprises at least about 80 wt % of ethane. In another aspect, the second C2 hydrocarbon stream comprises at least about 85 wt % of ethane. In yet another aspect, the second C2 hydrocarbon stream comprises at least about 90 wt % of ethane. In yet another aspect, the second C2 hydrocarbon stream comprises at least about 95 wt % of ethane. In yet another aspect, the second C2 hydrocarbon stream comprises at least from about 80 wt % to about 99 wt % of ethane.

The step of converting at least a portion of the ethane in the second C2 hydrocarbon stream to a second ethylene product can, for example, be performed by the ethane cracker disclosed herein. The step of converting at least a portion of the ethane in the second C2 hydrocarbon stream to a second ethylene product can, in another example, be performed by the ethane dehydrogenator disclosed herein.

In one aspect, the second ethylene product comprises at least about 80 wt % of ethylene. In another aspect, the second ethylene product comprises at least about 85 wt % of ethylene. In yet another aspect, the second ethylene product comprises at least about 90 wt % of ethylene. In yet another aspect, the second ethylene product comprises at least about 95 wt % of ethylene. In yet another aspect, the second ethylene product comprises at least from about 80 wt % to about 99 wt % of ethylene.

The step of producing ethylene oxide from at least a portion of the second ethylene product can be performed by the ethylene oxide reactor disclosed herein. In one aspect, at least about 80 wt % of the second ethylene product is converted to ethylene oxide. In another aspect, at least about 85 wt % of the second ethylene product is converted to ethylene oxide. In yet another aspect, at least about 90 wt % of the second ethylene product is converted to ethylene oxide. In yet another aspect, at least about 95 wt of second ethylene product is converted to ethylene oxide. In yet another aspect, at least about from 80 wt % to about 99 wt % of the second ethylene product is converted to ethylene oxide.

The step of combining at least a portion of the first ethylene product and at least a portion of the second ethylene product, thereby producing a third ethylene product can be performed by the seventh connector from the olefin separator to the ethylene oxide reactor as disclosed herein.

In one aspect, the third ethylene product comprises at least about 80 wt % of ethylene. In another aspect, the third ethylene product comprises at least about 85 wt of ethylene. In yet another aspect, the third ethylene product comprises at least about 90 wt % of ethylene. In yet another aspect, the third ethylene product comprises at least about 95 wt % of ethylene. In yet another aspect, the third ethylene product comprises at least from about 80 wt % to about 99 wt % of ethylene.

The step of producing ethylene oxide from at least a portion of the third ethylene product can be performed by the ethylene oxide reactor disclosed herein. In one aspect, at least about 80 wt % of the third ethylene product is converted to ethylene oxide. In another aspect, at least about 85 wt % of the third ethylene product is converted to ethylene oxide. In yet another aspect, at least about 90 wt % of the third ethylene product is converted to ethylene oxide. In yet another aspect, at least about 95 wt % of the third ethylene product is converted to ethylene oxide. In yet another aspect, at least about from 80 wt % to about 99 wt % of the third ethylene product is converted to ethylene oxide.

The step of producing ethylene glycol from at least a portion of the ethylene oxide can be performed in the ethylene glycol reactor disclosed herein. In one aspect, at least about 80 wt % of the ethylene oxide is converted to ethylene glycol. In another aspect, at least about 85 wt % of the ethylene oxide is converted to ethylene glycol. In yet another aspect, at least about 90 wt % of the ethylene oxide is converted to ethylene glycol. In yet another aspect, at least about 95 wt % of the ethylene oxide is converted to ethylene glycol. In yet another aspect, at least about from 80 wt % to about 99 wt % of the ethylene oxide is converted to ethylene glycol.

The step of producing one or more ethanolamines comprising monoethanolamine, diethanolamine, or triethanolamine, or a combination thereof from at least a portion of the ethylene oxide can be performed in the ethanolamine reactor disclosed herein. In one aspect, at least about 80 wt % of the ethylene oxide is converted to the one or more ethanolamines comprising monoethanolamine, diethanolamine, or triethanolamine, or a combination thereof. In another aspect, at least about 85 wt % of the ethylene oxide is converted to the one or more ethanolamines comprising monoethanolamine, diethanolamine, or triethanolamine, or a combination thereof. In yet another aspect, at least about 90 wt % of the ethylene oxide is converted to the one or more ethanolamines comprising monoethanolamine, diethanolamine, or triethanolamine, or a combination thereof. In yet another aspect, at least about 95 wt % the ethylene oxide is converted to the one or more ethanolamines comprising monoethanolamine, diethanolamine, or triethanolamine, or a combination thereof. In yet another aspect, at least about from 80 wt % to about 99 wt % of the ethylene oxide is converted to the one or more ethanolamines comprising monoethanolamine, diethanolamine, or triethanolamine, or a combination thereof.

In one aspect, at least about 80 wt % of the ethylene oxide is converted to monoethanolamine. In another aspect, at least about 85 wt % of the ethylene oxide is converted to monoethanolamine. In yet another aspect, at least about 90 wt % of the ethylene oxide is converted to monoethanolamine. In yet another aspect, at least about from 80 wt % to about 99 wt % of the ethylene oxide is converted to monoethanolamine.

In one aspect, at least about 10 wt % of the ethylene oxide is converted to diethanolamine. In another aspect, at least about 30 wt % of the ethylene oxide is converted to diethanolamine. In yet another aspect, at least about 50 wt % of the ethylene oxide is converted to diethanolamine. In yet another aspect, at least about from 10 wt % to about 99 wt % of the ethylene oxide is converted to diethanolamine.

In one aspect, at least about 10 wt % of the ethylene oxide is converted to triethanolamine. In another aspect, at least about 30 wt % of the ethylene oxide is converted to triethanolamine. In yet another aspect, at least about 50 wt % of the ethylene oxide is converted to triethanolamine. In yet another aspect, at least about from 10 wt % to about 99 wt % of the ethylene oxide is converted to triethanolamine.

In one aspect, the method can produce at least 100 liters of ethylene oxide per hour. In another aspect, the method can produce at least 500 liters of ethylene oxide per hour. In yet another aspect, the method can produce at least 1,000 liters of ethylene oxide per hour. In yet another aspect, the method can produce at least 10,000 liters of ethylene oxide per hour. For example, the method can produce from 100 to 10,000 liters of ethylene oxide per hour.

In one aspect, the method can produce at least 100 liters of ethylene glycol per hour. In another aspect, the method can produce at least 500 liters of ethylene glycol per hour. In yet another aspect, the method can produce at least 1,000 liters of ethylene glycol per hour. In yet another aspect, the method can produce at least 10,000 liters of ethylene glycol per hour. For example, the method can produce from 100 to 10,000 liters of ethylene glycol per hour.

In one aspect, the method can produce at least 100 liters of one or more ethanolamines per hour. In another aspect, the method can produce at least 500 liters of one or more ethanolamines per hour. In yet another aspect, the method can produce at least 1,000 liters of one or more ethanolamines per hour. In yet another aspect, the method can produce at least 10,000 liters of one or more ethanolamines per hour. For example, the method can produce from 100 to 10,000 liters of one or more ethanolamines per hour.

In one aspect, the method can produce at least 100 liters of monoethanolamine per hour. In another aspect, the method can produce at least 500 liters of monoethanolamine per hour. In yet another aspect, the method can produce at least 1,000 liters of monoethanolamine per hour. In yet another aspect, the method can produce at least 10,000 liters of monoethanolamine per hour. For example, the method can produce from 100 to 10,000 liters of monoethanolamine per hour.

In one aspect, the method can produce at least 100 liters of diethanolamine per hour. In another aspect, the method can produce at least 500 liters of diethanolamine per hour. In yet another aspect, the method can produce at least 1,000 liters of diethanolamine per hour. In yet another aspect, the method can produce at least 10,000 liters of diethanolamine per hour. For example, the method can produce from 100 to 10,000 liters of diethanolamine per hour.

In one aspect, the method can produce at least 100 liters of triethanolamine per hour. In another aspect, the method can produce at least 500 liters of triethanolamine per hour. In yet another aspect, the method can produce at least 1,000 liters of triethanolamine per hour. In yet another aspect, the method can produce at least 10,000 liters of triethanolamine per hour. For example, the method can produce from 100 to 10,000 liters of triethanolamine per hour.

5. Aspects

In view of the described catalyst and catalyst compositions and methods and variations thereof, herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the first C2 hydrocarbon stream, thereby producing a second C2 hydrocarbon stream; d) converting at least a portion of the ethane in the second C2 hydrocarbon stream to a second ethylene product; and e) producing ethylene oxide from at least a portion of the second ethylene product.

Aspect 2: The method of aspect 1, wherein the hydrocarbon stream comprises at least about 5 wt % of the first C2 hydrocarbon stream.

Aspect 3: The method of aspect 1, wherein the hydrocarbon stream comprises at least about 10 wt % of the first C2 hydrocarbon stream.

Aspect 4: The method of aspect 1, wherein the hydrocarbon stream comprises at least about 20 wt % of the first C2 hydrocarbon stream.

Aspect 5: The method of aspect 1, wherein the hydrocarbon stream comprises from about 10 wt % to about 30 wt % of the first C2 hydrocarbon stream.

Aspect 6: The method of any one of aspects 1-5, wherein the first C2 hydrocarbon stream comprises from about 20 wt % to about 70 wt % of ethane and from about 70 wt % to about 20 wt % of the first ethylene product.

Aspect 7: The method of any one of aspects 1-6, wherein the second C2 hydrocarbon stream comprises at least about 80 wt of ethane.

Aspect 8: The method of any one of aspects 1-7, wherein the hydrocarbon stream further comprises from about 30 wt % to about 70 wt % of C3-C10 hydrocarbons.

Aspect 9: The method of any one of aspects 1-8, wherein the method further comprises the step of producing ethylene glycol from at least a portion of the ethylene oxide.

Aspect 10: The method of any one of aspects 1-8, wherein the method further comprises the step of producing one or more ethanolamines comprising monoethanolamine, diethanolamine, and/or triethanolamine from at least a portion of the ethylene oxide.

Aspect 11: The method of aspect 10, wherein the one or more ethanolamines comprises at least 30 wt % of monoethanolamine.

Aspect 12: The method of aspect 10, wherein the one or more ethanolamines comprises at least 30 wt % of diethanolamine.

Aspect 13: The method of aspect 10, wherein the one or more ethanolamines comprises at least 30 wt % of triethanolamine.

Aspect 14: The method of any one of aspects 10-13, wherein the method further comprises the step of separating monoethanolamine from the one or more ethanolamines.

Aspect 15: The method of any one of aspects 10-14, wherein the method further comprises the step of separating diethanolamine from the one or more ethanolamines.

Aspect 16: The method of any one of aspects 10-15, wherein the method further comprises the step of separating triethanolamine from the one or more ethanolamines.

Aspect 17: The method of any one of aspects 1-16, wherein the step of converting at least a portion of the ethane in the second C2 hydrocarbon stream to a second ethylene product comprises dehydrogenating the at least a portion of the ethane in the second C2 hydrocarbon stream.

Aspect 18: The method of any one of aspects 1-16, wherein the step of converting at least a portion of the ethane in the second C2 hydrocarbon stream to a second ethylene product comprises cracking the at least a portion of the ethane in the second C2 hydrocarbon stream.

Aspect 19: The method of any one of aspects 1-18, wherein the step of producing ethylene oxide from at least a portion of the second ethylene product comprises reacting the second ethylene product with an oxygenate.

Aspect 20: A method comprising the steps of: a) producing a hydrocarbon stream from syngas via a Fischer-Tropsch reaction, wherein the hydrocarbon stream comprises a first C2 hydrocarbon stream comprising ethane and a first ethylene product; b) separating at least a portion of the first C2 hydrocarbon stream from the hydrocarbon stream; c) separating at least a portion of the first ethylene product from the C2 hydrocarbon stream, thereby producing a second C2 hydrocarbon stream; d) converting at least a portion the ethane in the second C2 hydrocarbon stream to a second ethylene product; e) combining at least a portion of the first ethylene product and at least a portion of the second ethylene product, thereby producing a third ethylene product; and f) producing ethylene oxide from at least a portion of the third ethylene product.

Aspect 21: The method of aspect 20, wherein the hydrocarbon stream comprises at least about 5 wt % of the first C2 hydrocarbon stream.

Aspect 22: The method of aspect 20, wherein the hydrocarbon stream comprises at least about 10 wt % of the first C2 hydrocarbon stream.

Aspect 23: The method of aspect 20, wherein the hydrocarbon stream comprises at least about 20 wt % of the first C2 hydrocarbon stream.

Aspect 24: The method of aspect 20, wherein the hydrocarbon stream comprises from about 10 wt % to about 30 wt % of the C2 hydrocarbon stream.

Aspect 25: The method of any one of aspects 20-24, wherein the first C2 hydrocarbon stream comprises from about 30 wt % to about 70 wt % of ethane and from about 70 wt % to about 30 wt % of the first ethylene product.

Aspect 26: The method of any one of aspects 20-25, wherein the second C2 hydrocarbon stream comprises at least about 80 wt % of ethane.

Aspect 27: The method of any one of aspects 20-26, wherein the hydrocarbon stream further comprises from about 30 wt % to about 70 wt % of C3-C10 hydrocarbons.

Aspect 28: The method of any one of aspects 20-27, wherein the method further comprises the step of producing ethylene glycol from at least a portion of the ethylene oxide.

Aspect 29: The method of any one of aspects 20-28, wherein the method further comprises the step of producing one or more ethanolamines comprising monoethanolamine, diethanolamine, and/or triethanolamine from at least a portion of the ethylene oxide.

Aspect 30: The method of aspect 29, wherein the one or more ethanolamines comprises at least 30 wt % of monoethanolamine.

Aspect 31: The method of aspect 29, wherein the one or more ethanolamines comprises at least 30 wt % of diethanolamine.

Aspect 32: The method of aspect 29, wherein the one or more ethanolamines comprises at least 30 wt % of triethanolamine.

Aspect 33: The method of any one of aspects 29-32, wherein the method further comprises the step of separating monoethanolamine from the one or more ethanolamines.

Aspect 34: The method of any one of aspects 29-33, wherein the method further comprises the step of separating diethanolamine from the one or more ethanolamines.

Aspect 35: The method of any one of aspects 29-34, wherein the method further comprises the step of separating triethanolamine from the one or more ethanolamines.

Aspect 36: The method of any one of aspects 20-35 wherein the step of converting at least a portion of the ethane in the second C2 hydrocarbon stream to a second ethylene product comprises dehydrogenating the at least a portion of the ethane in the second C2 hydrocarbon stream.

Aspect 37: The method of any one of aspects 20-35, wherein the step of converting at least a portion of the ethane in the second C2 hydrocarbon stream to a second ethylene product comprises cracking the at least a portion of the ethane in the second C2 hydrocarbon stream.

Aspect 38: The method of any one of aspects 20-37, wherein the step of producing ethylene oxide from at least a portion of the third ethylene product comprises reacting the third ethylene product with an oxygenate.

Aspect 39: A system comprising: a) a Fischer-Tropsch reactor comprising a first inlet and a first outlet; b) a deethanizer comprising a second inlet and a second outlet; c) an olefin separator comprising a third inlet and a third outlet; d) an ethane cracker comprising a fourth inlet and a fourth outlet or an ethane dehydrogenator comprising a fifth inlet and a fifth outlet; and e) an ethylene oxide reactor comprising a sixth inlet and a sixth outlet, wherein the Fischer-Tropsch reactor is in fluid communication with the deethanizer via a first connector, wherein the first connector is connected to the first outlet of the Fischer-Tropsch reactor and to the second inlet of the deethanizer, wherein the deethanizer is in fluid communication with the olefin separator via a second connector, wherein the second connector is connected to the second outlet of the deethanizer and to the third inlet of the olefin separator, wherein the olefin separator is in fluid communication with the ethane cracker or the ethane dehydrogenator via a third connector, wherein the third connector is connected to the third outlet of the olefin separator and to the fourth inlet of the ethane cracker or to the fifth inlet of the ethane dehydrogenator, wherein the ethane cracker or the ethane dehydrogenator is in fluid communication with the ethylene oxide reactor via a fourth connector, wherein the fourth connector is connected to the fourth outlet of the ethane cracker or to the fifth outlet of the ethane dehydrogenator and to the sixth inlet of the ethylene oxide reactor.

Aspect 40: The system of aspect 39, wherein the system comprises an ethane cracker.

Aspect 41: The system of aspect 39, wherein the system comprises an ethane dehydrogenator.

Aspect 42: The system of any one of aspects 39-41, wherein the system further comprises an ethylene glycol reactor comprising a seventh inlet, wherein the ethylene glycol reactor is in fluid communication with the ethylene oxide reactor via a fifth connector, wherein the fifth connector is connected to the sixth outlet of the ethylene oxide reactor and the seventh inlet of the ethylene glycol reactor.

Aspect 43: The system of any one of aspects 39-41, wherein the system further comprises an ethanolamine reactor comprising a tenth inlet, wherein the ethanolamine reactor is in fluid communication with the ethylene oxide reactor via an eighth connector, wherein the eighth connector is connected to the sixth outlet of the ethylene oxide reactor and the tenth inlet of the ethanolamine reactor.

Aspect 44: The system of any one of aspects 39-43, wherein the system further comprises a syngas production reactor comprising an eighth outlet, wherein the syngas production reactor is in fluid communication with the Fischer-Tropsch reactor via sixth connector, wherein the Fischer-Tropsch reactor further comprises a ninth inlet, wherein the sixth connector is connected to the eighth outlet of the syngas production reactor and to the ninth inlet of the Fischer-Tropsch reactor.

Aspect 45: The system of any one of aspects 39-44, wherein the olefin separator is in fluid communication with the ethylene oxide reactor via a seventh connector.

Aspect 46: The system of any one of aspects 39-45, wherein the system is on an industrial scale.

What is claimed is:

1. A method comprising the steps of:
    producing a hydrocarbon stream from syngas via a Fischer-Tropsch reaction, wherein the hydrocarbon stream comprises a first C2 hydrocarbon stream comprising ethane and a first ethylene product;
    separating at least a portion of the first C2 hydrocarbon stream from the hydrocarbon stream;
    separating at least a portion of the first ethylene product from the first C2 hydrocarbon stream, thereby producing a second C2 hydrocarbon stream;
    converting at least a portion of the ethane in the second C2 hydrocarbon stream to a second ethylene product;
    combining the first ethylene product and the second ethylene product, thereby producing a third ethylene product; and
    producing ethylene oxide from at least a portion of the third ethylene product.

2. The method of claim 1, wherein the first C2 hydrocarbon stream comprises from about 30 wt % to about 70 wt % of ethane and from about 70 wt % to about 30 wt % of the first ethylene product.

3. The method of claim 1, wherein the second C2 hydrocarbon stream comprises at least about 80 wt % of ethane.

4. The method of claim 1, wherein the hydrocarbon stream further comprises from about 30 wt % to about 70 wt % of C3-C10 hydrocarbons.

5. The method of claim 1, wherein the method further comprises the step of producing ethylene glycol from at least a portion of the ethylene oxide.

6. The method of claim 1, wherein the method further comprises the step of producing one or more ethanolamines comprising monoethanolamine, diethanolamine, and/or triethanolamine from at least a portion of the ethylene oxide.

7. The method of claim 6, wherein the method further comprises the step of separating monoethanolamine from the one or more ethanolamines.

8. The method of claim 6, wherein the method further comprises the step of separating diethanolamine from the one or more ethanolamines.

9. The method of claim 6, wherein the method further comprises the step of separating triethanolamine from the one or more ethanolamines.

10. The method of claim 1, wherein the step of converting at least a portion of the ethane in the second C2 hydrocarbon stream to a second ethylene product comprises dehydrogenating the at least a portion of the ethane in the second C2 hydrocarbon stream.

11. The method of claim 1, wherein the step of converting at least a portion of the ethane in the second C2 hydrocarbon stream to a second ethylene product comprises cracking the at least a portion of the ethane in the second C2 hydrocarbon stream.

12. The method of claim 1, wherein the step of producing ethylene oxide from at least a portion of the third ethylene product comprises reacting the third ethylene product with an oxygenate.

13. The method of claim 1, wherein the step of converting at least a portion of the ethane in the second C2 hydrocarbon stream to the second ethylene product consists of only producing the second ethylene product from the ethane in the second C2 hydrocarbon stream.

14. The method of claim 1, wherein the step of separating at least a portion of the first C2 hydrocarbon stream from the hydrocarbon stream is performed in a deethanizer.

* * * * *